United States Patent

Chornenky

[11] Patent Number: 6,108,402
[45] Date of Patent: Aug. 22, 2000

[54] DIAMOND VACUUM HOUSING FOR MINIATURE X-RAY DEVICE

[75] Inventor: Victor I. Chornenky, Minnetonka, Minn.

[73] Assignee: Medtronic Ave, Inc., Santa Rosa, Calif.

[21] Appl. No.: 09/008,202

[22] Filed: Jan. 16, 1998

[51] Int. Cl.[7] .................................................. H61J 35/32
[52] U.S. Cl. .............................. 378/119; 378/65; 378/121
[58] Field of Search ..................................... 378/119, 121, 378/65

[56] References Cited

U.S. PATENT DOCUMENTS

| Re. 34,421 | 10/1993 | Parker et al. ........................... 378/121 |
| 1,786,373 | 12/1930 | Walker . |
| 1,881,448 | 10/1932 | Forde et al. . |
| 2,467,812 | 4/1949 | Clapp . |
| 2,766,385 | 10/1956 | Herrnring et al. . |
| 3,005,096 | 10/1961 | Chynoweth . |
| 3,073,960 | 1/1963 | Guentner et al. . |
| 3,125,679 | 3/1964 | Ohde et al. . |
| 3,256,439 | 6/1966 | Dyke et al. . |
| 3,348,051 | 10/1967 | Weighart et al. . |
| 3,381,129 | 4/1968 | Duftschmid . |
| 3,388,314 | 6/1968 | Gould . |
| 3,484,721 | 12/1969 | Bond et al. . |
| 3,508,059 | 4/1970 | Vanderpool . |
| 3,538,919 | 11/1970 | Meyer . |
| 3,564,251 | 2/1971 | Youmans . |
| 3,617,939 | 11/1971 | Bond et al. . |
| 3,628,021 | 12/1971 | MacDonald . |
| 3,691,417 | 9/1972 | Gralenski . |
| 3,714,486 | 1/1973 | McCrary . |
| 3,752,990 | 8/1973 | Fischer . |
| 3,866,050 | 2/1975 | Whitfield . |
| 3,878,394 | 4/1975 | Golden . |
| 3,883,760 | 5/1975 | Cunningham, Jr. . |
| 3,920,999 | 11/1975 | Drexler et al. . |
| 3,970,884 | 7/1976 | Golden . |
| 3,987,281 | 10/1976 | Hodes . |
| 4,058,486 | 11/1977 | Mallozzi et al. . |
| 4,060,731 | 11/1977 | Rissi . |
| 4,097,759 | 6/1978 | Furbee et al. . |
| 4,104,526 | 8/1978 | Albert . |
| 4,104,530 | 8/1978 | Weiss . |
| 4,104,531 | 8/1978 | Weiss . |

(List continued on next page.)

FOREIGN PATENT DOCUMENTS

| 2054738 | 5/1972 | Germany . |
| 26 08 418 | 9/1977 | Germany . |
| 58-145098 | 8/1983 | Japan . |
| 814331 | 3/1981 | Russian Federation . |
| WO 95/20241 | 7/1995 | WIPO . |
| WO 96/02059 | 1/1996 | WIPO . |
| WO 97/07740 | 3/1997 | WIPO . |

OTHER PUBLICATIONS

Anthony, T., "Cylindrically symmetric diamond parts by hot–filament CVD", *Diamond And Related Materials*, vol. 6, pp. 1707–1715 (1997).

PCT International Search Report (English Translation Abstract of PCT/US96/13629 included) (4 pages).

Brochure: "Dunlee DL–1 Stationary Anode Insert", Dunlee Corporation, Bellwood, IL 60104, Jun. 1972.

Wiedermann, et al., "Effects of high–dose intracoronary irradiation on vasomotor function and smooth muscle histopathology", pp. H125–H132 (1994).

*Primary Examiner*—David P. Porta
*Assistant Examiner*—Drew A. Dunn

[57] ABSTRACT

A device suitable for insertion into a body and for delivery of x-ray radiation, comprising a connector, a diamond vacuum housing coupled to a distal portion of the connector, an anode and cathode, disposed within the vacuum housing and arranged to enable the production of x-ray radiation. Also, a device suitable for insertion into a body and for delivery of x-ray radiation including a vacuum housing coupled to a distal portion of a connector where the vacuum housing has a diameter of less than 2.5 mm. A method of fabricating a miniature x-ray emitter by constructing a structure of diamond that defines a vacuum chamber and encases a cathode and an anode.

20 Claims, 2 Drawing Sheets

U.S. PATENT DOCUMENTS

| | | |
|---|---|---|
| 4,104,532 | 8/1978 | Weiss . |
| 4,109,154 | 8/1978 | Taumann . |
| 4,117,334 | 9/1978 | Strauts . |
| 4,143,275 | 3/1979 | Mallozzi et al. . |
| 4,158,138 | 6/1979 | Hellstrom . |
| 4,163,901 | 8/1979 | Azam et al. . |
| 4,191,193 | 3/1980 | Seo . |
| 4,344,181 | 8/1982 | Baecklund . |
| 4,359,660 | 11/1982 | Smith et al. . |
| 4,368,538 | 1/1983 | McCorkle . |
| 4,563,769 | 1/1986 | Madsen . |
| 4,607,380 | 8/1986 | Oliver . |
| 4,636,195 | 1/1987 | Wolinksy . |
| 4,646,338 | 2/1987 | Skillicorn . |
| 4,669,467 | 6/1987 | Willett et al. . |
| 4,670,894 | 6/1987 | Birnbach et al. . |
| 4,694,480 | 9/1987 | Skillicorn . |
| 4,701,941 | 10/1987 | Szirmai et al. . |
| 4,702,228 | 10/1987 | Russell, Jr. et al. . |
| 4,715,054 | 12/1987 | Kato et al. . |
| 4,763,671 | 8/1988 | Goffinet . |
| 4,789,997 | 12/1988 | Madsen et al. . |
| 4,794,931 | 1/1989 | Yock . |
| 4,800,581 | 1/1989 | Kujirai et al. . |
| 4,824,436 | 4/1989 | Wolinsky . |
| 4,856,036 | 8/1989 | Malcolm et al. . |
| 4,913,142 | 4/1990 | Kittrell et al. . |
| 4,924,485 | 5/1990 | Hoeberling . |
| 4,966,596 | 10/1990 | Kuntz et al. . |
| 4,976,266 | 12/1990 | Huffman et al. . |
| 4,979,199 | 12/1990 | Cueman et al. . |
| 5,042,486 | 8/1991 | Pfeiler et al. . |
| 5,059,166 | 10/1991 | Fischell et al. . |
| 5,077,771 | 12/1991 | Skillicorn et al. . |
| 5,087,244 | 2/1992 | Wolinsky et al. . |
| 5,090,043 | 2/1992 | Parker et al. .......................... 378/122 |
| 5,099,845 | 3/1992 | Besz et al. . |
| 5,101,422 | 3/1992 | Thiel et al. . |
| 5,106,360 | 4/1992 | Ishiwara et al. . |
| 5,148,463 | 9/1992 | Woodruff et al. . |
| 5,153,900 | 10/1992 | Nomikos et al. . |
| 5,165,093 | 11/1992 | Miller et al. . |
| 5,199,939 | 4/1993 | Dake et al. . |
| 5,222,116 | 6/1993 | Eloff et al. . |
| 5,228,176 | 7/1993 | Bui et al. . |
| 5,264,801 | 11/1993 | Decou, Jr. et al. . |
| 5,290,275 | 3/1994 | Kittrell et al. . |
| 5,313,949 | 5/1994 | Yock . |
| 5,313,950 | 5/1994 | Ishikawa et al. . |
| 5,342,283 | 8/1994 | Good . |
| 5,364,336 | 11/1994 | Carr . |
| 5,369,679 | 11/1994 | Sliski et al. . |
| 5,402,790 | 4/1995 | Jang et al. . |
| 5,414,748 | 5/1995 | Upadhya . |
| 5,422,926 | 6/1995 | Smith et al. . |
| 5,425,735 | 6/1995 | Rosen et al. . |
| 5,428,658 | 6/1995 | Oettinger et al. . |
| 5,437,277 | 8/1995 | Dumoulin et al. . |
| 5,442,678 | 8/1995 | Dinsmore et al. . |
| 5,444,254 | 8/1995 | Thomson . |
| 5,452,720 | 9/1995 | Smith et al. . |
| 5,453,575 | 9/1995 | O'Donnell et al. . |
| 5,454,809 | 10/1995 | Janssen . |
| 5,465,732 | 11/1995 | Abele . |
| 5,469,490 | 11/1995 | Golden et al. . |
| 5,474,075 | 12/1995 | Goldberg et al. . |
| 5,503,613 | 4/1996 | Weinberger . |
| 5,504,799 | 4/1996 | Suzuki . |
| 5,511,107 | 4/1996 | Sliski . |
| 5,528,652 | 6/1996 | Smith et al. . |
| 5,566,221 | 10/1996 | Smith et al. . |
| 5,621,780 | 4/1997 | Smith et al. . |
| 5,623,139 | 4/1997 | Sliski . |
| 5,635,709 | 6/1997 | Sliski et al. . |
| 5,729,583 | 3/1998 | Tang et al. ............................. 378/122 |
| 5,748,699 | 5/1998 | Smith . |
| 5,854,822 | 12/1998 | Chornenky et al. .................... 378/122 |

DIAMOND VACUUM HOUSING FOR MINIATURE X-RAY DEVICE

FIELD OF THE INVENTION

The present invention is directed to a miniature x-ray device arrangement, and more particularly, to an arrangement for a housing for a miniature x-ray device.

BACKGROUND OF THE INVENTION

In the medical field, doctors and scientists are striving to find less invasive ways to treat patients. By using treatments that are less intrusive to the body, doctors can greatly reduce the stress on the patient's system and exposure to infection. For example, laparoscopic techniques enable physicians to explore the interior of the body and perform surgery through a small opening in the skin. Less intrusive medical techniques are extremely beneficial when applied to cardiovascular diseases, for example.

Cardiovascular diseases affect millions of people, frequently causing heart attacks and death. One common aspect of many cardiovascular diseases is stenosis, or the thickening of the artery or vein, decreasing blood flow through the vessels. Angioplasty procedures have been developed to reopen clogged arteries without resorting to a bypass operation. However, in a large percentage of cases, arteries become occluded again after an angioplasty procedure. This recurrent decrease of the inner diameter of the vessel is termed restenosis. Restenosis frequently requires a second angioplasty and eventual bypass surgery. Bypass surgery is very stressful on a patient, requiring the chest to be opened, and presents risks from infection, anesthesia, and heart failure. Effective methods of preventing or treating restenosis could benefit millions of people.

One approach to restenosis has been attempted radiation of the vessel wall. For example, U.S. patent application Ser. No. 08/701,764, filed Aug. 22, 1996, titled "X-Ray Catheter," describes an x-ray device for insertion into a lumen of a body, capable of localized x-ray radiation. U.S. application Ser. No. 08/701,764 is hereby incorporated by reference in its entirety. There are many difficult technical issues associated with delivering localized x-ray radiation to the interior of a patient's lumen. A U.S. patent application Ser. No. 08/900,609, now U.S. Pat. No. 5,854,822 titled "Miniature X-Ray Device Having Cold Cathode" discusses improved cathode configurations that improve the rate of electron emission and decrease the required electric field. Ser. No. 08/900,609 was filed on Jul. 25, 1997 and is incorporated herein by reference in its entirety.

Thus, there is a need for effective devices to be used to treat the interior of the body with minimal intrusion. Effective, less invasive techniques for preventing and treating stenosis and restenosis at a lumen wall are especially needed. Other applications for localized x-ray radiation are numerous, such as treating the interior of the esophagus, and providing radiation to tumors.

SUMMARY OF THE INVENTION

Generally, the present invention provides an improved housing material for a miniature x-ray emitter. In one particular embodiment of the invention, a device suitable for insertion into a body and delivering x-ray radiation includes a connector with a proximal and a distal portion; a diamond vacuum housing coupled to the distal portion of the connector; and an anode and a cathode disposed within the diamond vacuum housing.

A method of fabricating a miniature x-ray emitter is also shown, and includes the steps of constructing a structure of diamond, the structure of diamond defining a vacuum chamber and encasing a cathode and an anode.

BRIEF DESCRIPTION OF THE DRAWINGS

The invention may be more completely understood in consideration of the detailed description of the embodiment of the invention which follows in connection with the accompanying drawings in which.

Figure 1:
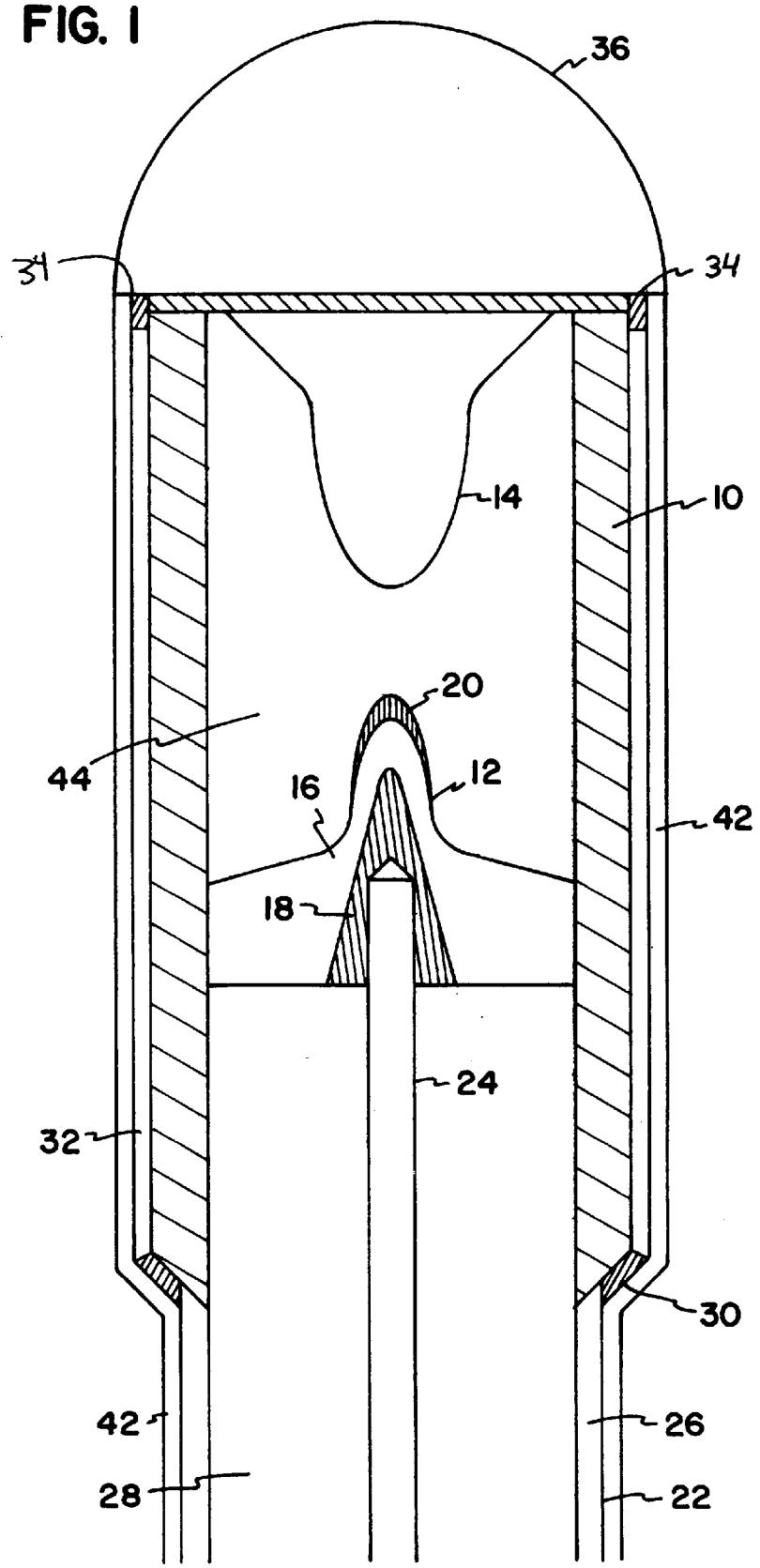
FIG. 1 shows an exploded cross-sectional view of an embodiment of a diamond housing for a miniature x-ray device of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the invention is to cover all modifications, equivalents, and alternatives falling within the spirit and scope of the invention as defined in the appended claims.

DESCRIPTION OF THE INVENTION

The present invention is applicable to a variety of devices, methods of use, systems and arrangements which irradiate lumens, vessels, or interior sites in a body with x-ray radiation. The invention is particularly advantageous in preventing restenosis in the cardiovascular system.

While the present invention is not so limited, an appreciation of various aspects of the invention is best seen through a discussion of various application examples operating in such an environment.

Generally, the present invention provides an improved housing material for a miniature x-ray emitter that is designed for use inside a patient's body, especially a cardiovascular system. A device according to the present invention is suitable for insertion into the body, delivers x-ray radiation, and includes a connector, such as a coaxial cable, with a proximal and a distal portion. The device also includes a diamond vacuum housing that is coupled to the distal portion of the coaxial cable. The diamond vacuum housing contains an anode and a cathode for producing x-ray radiation. The present invention also provides a method of fabricating a miniature x-ray emitter, including the steps of constructing a structure of diamond that defines a vacuum chamber and encases a cathode and an anode.

Miniature x-ray emitters require materials with stringent specification requirements for safe and effective operation within a body. For example, high potential differences are present within an x-ray emitter across very small distances. Considerable amounts of heat may also be produced within the x-ray unit. The components of the x-ray emitter must be capable of construction at very small scales in order to allow an x-ray emitter to enter a lumen of the patient, such as a blood vessel or artery. One x-ray device designed for use inside the body is described in U.S. patent application Ser. No. 08/701,764, filed Aug. 22, 1996, titled "X-Ray Catheter," which is hereby incorporated herein by reference in its entirety.

The total diameter of the x-ray emitter will be small enough to readily pass through human arteries and/or arterioles. In particular, the total diameter will be about 1–4 millimeters. As will be apparent in the description of the drawings to follow, at certain points in the x-ray device, the high-potential lead that is connected to the anode is separated from the low-potential lead that is connected to the cathode by a distance of a millimeter or less. It is preferable that a housing material of the x-ray emitter have a high dielectric strength, in order to withstand a large electrical field without breakdown. Other qualities of the emitter also contribute to prevent electrical breakdown, such as the geometry of the emitter, lack of gases and contaminants in the vacuum housing, resistivity, surface resistivity, and the dielectric constant, as is known in the art.

A cathode's "triple junction point" (the junction between the cathode, housing wall, and vacuum) may be screened from the high electrical field between the anode and the cathode by a conductive coating and/or the other components in order to reduce the chances of electrical flashover. The shell material may have a low dielectric constant, so that any spikes in the electric field are avoided.

Electrical current from the anode to the cathode along an inner wall or through an inner wall of the housing should be prevented. Therefore, in connection with the present invention, it has also been found that high resistivity is a desirable quality for the shell housing material to prevent leakage current through the housing. Leakage current through the housing will generate undesirable heat. In addition, current that is leaking through the housing is not being used to generate x-rays, so that an accurate x-ray dose may not be administered.

In addition, a high surface resistivity is a desired characteristic of the housing material. Preferably the housing has a surface resistivity of at least $10^{11}$ ohms per square. A surface resistivity of $10^{13}$ ohms per square or higher is more preferable. X-ray transparency is a desirable characteristic of the housing material. The housing surrounds the anode and cathode components, where the x-ray radiation is produced. X-ray transparent housing material allows consistent and full dosages to reach the patient's lumen.

A vacuum chamber is enclosed by the shell in the x-ray device. Therefore, it has been found that vacuum-tight connections are desired for proper operation of the x-ray device. The shell material used must therefore be capable of heat-resistant, vacuum-tight connections with the metal components and the anode and cathode.

It has been found that diamond is an attractive housing material choice for a miniature x-ray device. In connection with this invention, it has been found that a three-dimensional diamond structure is a superior housing material for a miniature x-ray emitter. Chemical vapor deposition (CVD) processing of diamond is one way to construct the housing of the present invention. Recent advances in CVD diamond techniques make it possible to create a three-dimensional diamond housing with an outer diameter of less than 2.5 mm.

FIG. 1 is a cross-sectional view of an x-ray unit in accordance with the present invention. The x-ray unit of FIG. 1 has a diamond vacuum housing 10, a diamond anode structure 12, and a cathode structure 14. Generally, many different elements could be used to guide the x-ray device of the present invention to the treatment site. For example, the x-ray unit can be positioned at the distal end of a flexible catheter shaft, not shown.

When a high potential difference is applied across the anode and cathode, electrons emitted by the cathode are accelerated across the gap separating the anode and cathode. The accelerated electrons collide with the anode, abruptly decelerating and emitting x-ray radiation by the Bremsstrahlung effect, as it is known in the art. As the x-ray radiation penetrates into the wall of the lumen, it damages the DNA of a majority of smooth muscle cells. As the population of undamaged smooth muscle cells is depleted, their proliferation rate during the healing process after an angioplasty procedure is inhibited, and the consequent restentosis does not occur. In coronary applications, it is desirable to have the x-ray radiation penetrate into the adventitia tissue of the blood-vessel about 1–2 millimeters deep from the inner vessel wall. Penetration into the cardiac muscle tissue should be minimized. It is further desirable to deliver x-ray radiation with a peak energy of about 8–12 kiloelectronvolts (keV) in coronary applications. When the desired dosage has been delivered, the voltage source is discontinued and the catheter withdrawn from the body.

According to the present invention, the vacuum housing 10 may be formed of chemically vapor deposited diamond. Diamond structures are stronger than the boron nitride structures previously used for x-ray catheters. The added strength of the diamond housing permits the construction of x-ray catheters with diameters less than 2.5 mm and in some embodiments less than 2 mm. Treatments for cardiovascular disease continue to become less invasive in the patient's body and therefore less stressful to the patient's system. Size improvements on an x-ray device reduce the size of the required incision, improve maneuverability, decrease the stress on the lumen, and enable the device to reach more remote locations in the patient's body. Constructing the vacuum housing with diamond permits a significant size reduction.

Diamond also has the attractive characteristic of being transparent to x-ray radiation, thereby allowing the full dosage of x-rays to reach the lumen wall. In addition, diamond is an excellent heat conductor. A certain amount of heat is typically generated by the x-ray unit at the anode. The thermal conductivity of diamond is 20 watts/cm° C. Therefore, the heat generated by the x-ray unit at the anode will be dissipated throughout the structure quickly, preventing damage to the anode components.

When used in an artery, where the typical blood flow is about 50–$cm^3$/minute, the blood flow aids in dissipating heat conducted through the vacuum housing. However, a cooling mechanism may still be desirable, especially when the x-ray emitter is used inside a flexible catheter shaft. A saline flush through the flexible catheter shaft, for example, carries away heat conducted through the vacuum housing so that the catheter itself will not be damaged by the heat. Where the x-ray device is used in other body systems, additional cooling methods may be required. A saline flush may also provide lubrication between the x-ray emitter assembly and the catheter sheath.

A further advantage of including diamond in the vacuum housing is the electrical resistivity of diamond. The electrical resistivity of chemically vapor-deposited diamond is approximately $10^{15}$ ohm-cm. The electric field at which diamond will experience electrical breakdown is $10^7$ V cm. In order to maintain an electric field at the surface of the cathode, the anode and high voltage carrying components of the x-ray unit must be insulated from the conductive coating and external conductive layer of the coaxial cable.

The potential of the external conductive layer is a floating low potential. The patient is grounded, as is known in the art and as is described in the "Handbook of Electrical Hazards and Accidents," edited by Leslie Geddes, published by CRC Press, Boca Raton, Fla., 1995, which is hereby incorporated herein by reference in its entirety. Insufficient insulation results in electrical discharge or flashover. The use of diamond as the vacuum housing improves insulation and reduces the likelihood of flashover.

Figure 2:
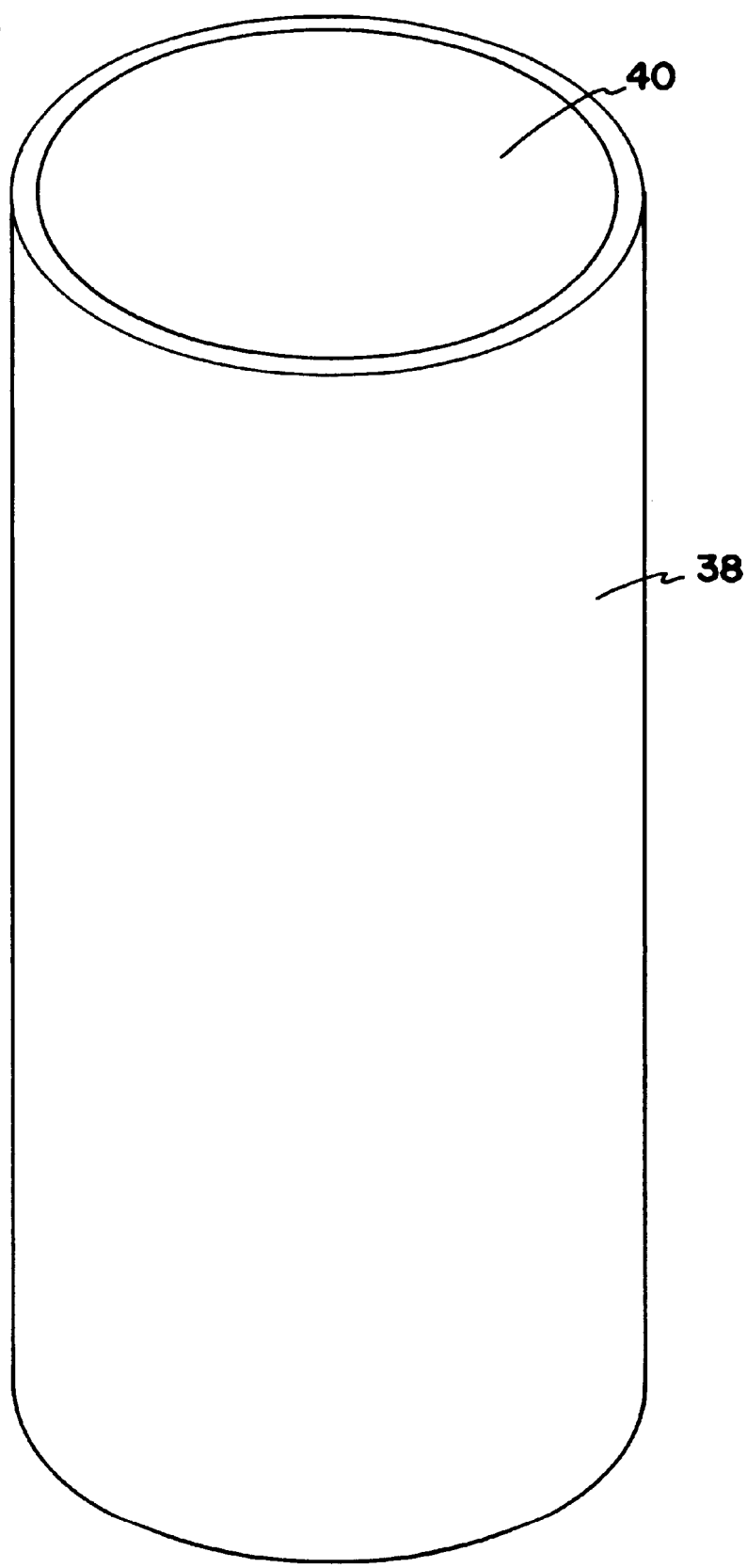
FIG. 2 shows a perspective view of a mandrel for use in chemical vapor deposition of the diamond housing.

The diamond vacuum housing may be formed by chemical vapor deposition. Recent advances in chemical vapor deposition techniques have made possible the construction of three-dimensional diamond structures. Thus, in accordance with this invention, it is possible to use a three-dimensional diamond shell as a structural element of the vacuum housing. Structural diamond tubes can be grown by depositing diamond onto a metal rod, or mandrel, as shown in FIG. 2. The mandrel 38 can be made of Tn, W, Mo, Ta, or Si. These materials are most preferred for diamond deposition because they do not react with the deposited diamond, and they are easy to eliminate when the deposition is complete. The most preferred methods of creating structural diamond parts are hot filament deposition, combustion, and direct current arc jets. These three types of chemical vapor deposition methods are described in the art and are generally known to those skilled in the art. For example, deposition of diamond tube shapes is well-described in "Cylindrically Symmetric Diamond Parts by Hot-Filament CVD," Diamond and Related Materials, Volume 6, pages 1707–1715 (1997), written by T. R. Anthony, which is incorporated herein by reference in its entirety.

The diamond housing 10 is preferably shaped as a hollow cylinder, requiring a cylindrical mandrel 38. A conically shaped housing may also be used. However, many other configurations for the diamond shell 10 are possible and contemplated by this invention.

The assembly of FIG. 2 is placed in a chemical vapor deposition (CVD) reactor for the deposition of diamond by CVD, as is known in the art. Chemical vapor deposition of diamond is also described, for example, in the book *Diamond Films and Coatings*, Editor Robert F. Davis, Noyes Publication, 1993, which is incorporated herein by reference in its entirety. CVD can be performed by General Electric and many other manufacturers.

The CVD reactor contains a plasma that is created using a power source such as direct current, high-frequency or microwave source. The plasma may be one to three percent $CH_4$ and ninety-seven to ninety-nine percent $H_2$. A three-dimensional diamond structure is deposited on the mandrel in a CVD diamond reactor chamber. Then, the mandrel may be eliminated by etching with an acid, as is known in the art. Only the three-dimensional diamond structure remains. A cylinder of diamond 100 to 200 microns thick is formed by the CVD process. After the diamond housing is formed, the housing is annealed at a temperature of about 700° C. for one to two hours in order to increase the electrical resistivity of the structure. The inner surface of the diamond housing may also be treated in order to increase electrical resistivity at that surface. Etching of the inner surface with an acid increases the electrical resistivity and therefore helps prevent a short in the x-ray emitter due to a discharge between the high-potential anode and the cathode which is at a low potential. An example of an acid that may be used is hydrofluoric acid.

The other components of the miniature x-ray emitter of the present invention will 15 now be described. Still referring to FIG. 1, the anode 12 may be a tapered cylinder with a rounded distal end. Many different types of material and different shape configurations may be used for the anode which are capable of decelerating electrons to produce x-ray radiation. For example, the anode structure may include either a solid diamond or a bell-shaped diamond sheath 16 covering a metal core 18. For example, the diamond covering 16 could be formed by a chemical vapor deposition to be approximately 50–100 microns thick on the metal core. The diamond covering 16 that may be used in the anode 12 may be conductive to at least some degree, in order to establish the high voltage that is carried by the center conductor 24 at the tip of the anode 12. In order to create a diamond structure with sufficient conductivity, in contrast to the typically electrically resistive diamond, the presence of some graphite bonds in the diamond structure may be used. A diamond film having some sp2 carbon bonds to facilitate conductivity is particularly suited for use in the present invention. Other elements may also be present in the diamond structure in small quantities. A diamond structure with resistivity of no more than $10^6$ ohm cm is preferred. A tip 20 of the diamond anode structure is coated with a heavy metal such as gold, tungsten, or platinum for more efficient production of x-ray radiation. Gold, platinum, and tungsten are sufficiently heavy to cause the incident electrons to generate the desired x-ray radiation. Platinum is most preferred for the material of tip 20 because it has the highest atomic number and a higher melting point.

The anode 12 may be secured to the interior of the vacuum housing 10 in many different ways. For example, the anode could be vacuum brazed to the interior of the vacuum housing 10. The vacuum housing 10 containing the anode 12 and the cathode 14 is operatively coupled to a connector, which provides the connection from the x-ray emitter to the outside of the patient's body. This connector could be a coaxial cable, for example, that delivers the required voltage to the x-ray emitter. Other connectors capable of supplying the anode 12 and the cathode 14 with the electrical potential may also be used and are contemplated by this invention. The connector may also include a catheter sheath, or a biocompatible coating.

Referring once again to FIG. 1, the cathode 14 is located at the distal portion of the x-ray catheter in this embodiment However, many different configurations for the anode and cathode are possible. For example, the cathode may be situated at the proximal end of the emitter. The cathode and anode may also be on opposing sides of the emitter. After the CVD process creating the housing is complete and the anode is attached, the cathode structure may be vacuum brazed to the open end of the diamond housing with brazing materials, sealing the vacuum chamber. Vacuum brazing is known in the art and can be provided by Koral Labs., Fridley, Minn., for example. After the vacuum brazing is complete, the anode and cathode may be separated by a vacuum gap about 0.25 mm wide in one embodiment.

In one embodiment the cathode structure comprises a cathode base and a thin diamond film located on the cathode base. Preferably, the cathode base may be a getter, and the diamond film could be applied directly to the getter. U.S. patent application Ser. No. 08/900,609, filed Jul. 25, 1997 and titled "Miniature X-Ray Device Having Cold Cathode," describes cathode configurations that include a diamond film. U.S. patent Ser. No. 08/900,609 is incorporated herein by reference in its entirety. The material used for the cathode base depends on how the diamond film is formed. The thin diamond film can be obtained by chemical vapor deposition, as is known in the art. Various materials may serve as an effective substrate for the diamond film synthesis by chemical vapor deposition, such as tungsten, molybdenum, and tantalum. As described more fully below, the diamond film could also be fabricated by other methods, such as by laser ion deposition, making a wider range of materials available for the base of the cathode, such as a getter.

The term diamond film, as used herein, contemplates a coating of carbon having diamond-like bonds which demonstrate negative electron affinity. It is also desirable to have sufficient conductivity to create a constant supply of electrons to the surface of the cathode. The presence of some graphite bonds in the diamond film will contribute to conductivity. Thus a combination of a diamond film having both sp3 carbon bonds, to function as a cathode, and some sp2 carbon bonds, to facilitate conductivity, is particularly suited for use in such a system. Other elements may also be present in the film in small quantities. The diamond film will have the property that it can emit electrons at electrical fields greater than or equal to about 20 V/micron. This required electric field is extremely low when compared to that required by metal emitters such as molybdenum or silicon, which require greater than 1,000 V/micron.

If a getter is a component of the cathode structure, the getter may aid in creating and maintaining a vacuum condition of high quality. The getter has an activation temperature, at which it will react with stray gas molecules in the vacuum. After the getter is disposed as part of the cathode structure within the vacuum housing and the housing pumped out, the device is heated to the activation temperature. It is desirable that the getter used have an activation temperature that is not so high that the x-ray device will be damaged when heated to the activation temperature. A SAES ST 101 alloy getter may be used, which has an activation temperature in the range 750 to 900° C. and is composed of approximately 64% zirconium and 16% aluminum. A ST 707 alloy getter could also be used, which has an activation temperature in the range 400 to 500° C. and is composed of approximately 70% zirconium, 24.6% vanadium, and 5.4% iron.

In one embodiment, the cathode 14 comprises a material that is a mixture of diamond powder and granulated getter material The diamond getter mixture type cathode is described more fully in U.S. Provisional Patent Application Ser. No. 60/055,682, filed Aug. 18, 1997 and titled "Cathode Using Getter Material," which is incorporated herein by reference in its entirety.

The connections between the components of the x-ray emitter will now be described. After the cathode structure has been vacuum brazed to the vacuum housing and the getter has been activated, the entire x-ray unit is coated with a conductive coating 32, such as a titanium coating having a thickness of 0.1 to 1 µm. In the alternative, a titanium coating over the housing could be itself coated with a layer of nickel and then a layer of gold. Gold provides a preferable outer coating because it does not oxidize and it is easy to work with. Although titanium does oxidize, it is self-cleaning when heated in a vacuum, so any oxidization may be easily removed. The coating is coupled to the cathode base and the external conductive layer of the coaxial cable 26 by conductive solder 34. Thus, all three elements, the external conductive layer of the coaxial cable 26, the conductive coating 32 and the cathode 14 can be at a low potential in order to create the potential difference necessary for electron acceleration.

FIG. 1 shows a connector 22 that is a coaxial cable. The coaxial cable includes a central core conductor 24 which is connected to the anode 12. The coaxial cable connector 22 also includes an outer conductor 26 for connection to the cathode 14. Within the coaxial cable connector 22, an insulative material 28 may separate the core conductor 24 from the outer conductor 26. Different types of connectors may also be used to provide high voltage to the x-ray emitter. For example, two wire conductive lines, round or flat wires, could serve as the connector 22. A connector that is able to conduct an electric current at 15–30 kV and above may be used as the connector 22.

The anode structure receives the distal end of a high voltage conductor, such as the core conductor 24 of a coaxial cable in this embodiment. The proximal end of the core conductor of the coaxial cable is connected to a high voltage power supply, not shown. A coronary artery after angioplasty typically has a diameter of only about 3.0 millimeters. Therefore, a coaxial cable and any covering used in this device must have a diameter less than or equal to 3.0 millimeters. The cable must also be able to carry the required voltages and have sufficient flexibility to make numerous sharp turns as it follows the artery path. Standard high voltage coaxial cables are generally not flexible enough. However, miniature high frequency coaxial cables with an outer diameter of approximately 1.0 millimeters to 3.0 millimeters are available which exhibit sufficient flexibility. These cables can hold direct current voltages as high as 75–100 kV without breakdown. Such cables are manufactured by, for example, New England Electric Wire Corporation, Lisbon, N.H.

The outer conductor 26 must be electrically connected to the cathode 14, so that an electric field will be applied across the cathode 14 and the anode 12 causing electrons to be emitted from the cathode 14. The conductive coating 32 is situated on the outside of the diamond shell 10. The conductive coating 32 is connected to the outer conductor 26 by conductive soldering 30, at the juncture between the proximal end of the diamond housing 10 and the connector 22. Conductive coating 32 is in turn electrically coupled to the cathode 14 by a second area of conductive soldering 34.

At the distal end of the diamond shell 10, a soft distal tip 36 may be utilized to improve maneuverability through a patient lumen. The distal tip 36 may be made of any biocompatible, flexible material, such as polyurethane, polyethylene, or Teflon® material.

A coating 42 of biocompatible material may be applied to the entire x-ray unit, such as polyethylene, polyurethane or Teflon® material. A thickness of less than about 0.002 inches is preferred so that the overall outer diameter is not increased significantly.

The various embodiments described above are provided by way of illustration only and should not be construed to limit the invention. Those skilled in the art will readily recognize various modifications and changes which may be made to the present invention without strictly following the exemplary embodiments and applications illustrated and described herein, and without departing from the true spirit and scope of the present invention which is set forth in the following claims.

I claim:

1. A device suitable for insertion into a body and for delivery of x-ray radiation, comprising:
   a connector, including a proximal and a distal portion;
   a diamond vacuum housing coupled to the distal portion of the connector;
   an anode disposed within the diamond vacuum housing; and
   a cathode disposed within the diamond vacuum housing, the cathode and the anode being arranged to enable the production of x-ray radiation.

2. The device of claim 1 the diamond vacuum housing being formed by chemical vapor deposition.

3. The device of claim 1 the cathode being comprised of diamond.

4. The device of claim 1 the cathode being comprised of diamond deposited on a getter material.

5. The device of claim 1 the cathode being comprised of diamond deposited on a metal.

6. The device of claim 1 the cathode being comprised of the diamond deposited on molybdenum.

7. The device of claim 1 the anode being comprised of a heavy metal.

8. The device of claim 1 the anode being comprised of gold.

9. The device of claim 1 the anode being comprised of tungsten.

10. The device of claim 1 the anode being comprised of a diamond inner portion.

11. The device of claim 1 the anode being comprised of a metal core, an inner portion of diamond over the metal core, and a tip portion of a heavy metal.

12. The device of claim 1 wherein the connector is a coaxial cable.

13. The device of claim 1 further comprising a biocompatible coating over the diamond housing.

14. The device of claim 1 wherein the diamond vacuum housing comprises an external surface and a conductive coating on the external surface of the diamond vacuum housing, wherein the conductive coating is electrically connected to the cathode.

15. A device suitable for insertion into a body and for delivery of X-ray radiation, comprising:

a connector, including a proximal and a distal portion, the connector conductive for an electric current at voltages above 10 kilovolts;

a diamond vacuum housing coupled to the distal portion of the connector, the vacuum housing having a diameter less than 2.5 millimeters;

an anode disposed within the vacuum housing; and a cathode disposed within the vacuum housing, the cathode and the anode being arranged to enable the production of X-ray radiation.

16. A method of fabricating a miniature x-ray emitter for use in a catheter by constructing a structure of diamond, the structure of diamond defining a vacuum chamber and encasing a cathode and an anode, the cathode being operative with the anode to produce x-ray radiation.

17. The method of claim 16 wherein the diamond structure is formed by chemical vapor deposition.

18. The method of claim 16 wherein the structure of diamond supports the cathode and the anode.

19. The method of claim 16 wherein the structure of diamond insulates the cathode, the anode, and the vacuum chamber to prevent electrical discharge during operation at high voltages.

20. The method of claim 16 further comprising forming a conductive coating on an external surface of the structure of diamond wherein the conductive coating is electrically connected to the cathode.

\* \* \* \* \*